(12) United States Patent
Fang et al.

(10) Patent No.: US 8,722,951 B2
(45) Date of Patent: May 13, 2014

(54) FUEL COMPOSITION

(71) Applicant: Primus Green Energy Inc., Hillsborough, NJ (US)

(72) Inventors: Howard L. Fang, Bridgewater, NJ (US); Meifang Qin, Princton, NJ (US); Moshe Ben-Reuven, Princeton, NJ (US)

(73) Assignee: Primus Green Energy Inc., Hillsborough, NJ (US)

( * ) Notice: Subject to any disclaimer, the term of this patent is extended or adjusted under 35 U.S.C. 154(b) by 0 days.

(21) Appl. No.: 13/940,981

(22) Filed: Jul. 12, 2013

(65) Prior Publication Data

US 2014/0018587 A1 Jan. 16, 2014

Related U.S. Application Data

(62) Division of application No. 13/547,826, filed on Jul. 12, 2012, now Pat. No. 8,569,554.

(51) Int. Cl.
*C07C 1/04* (2006.01)
*C07C 1/207* (2006.01)

(52) U.S. Cl.
USPC ............ 585/401; 585/701; 585/323; 585/319

(58) Field of Classification Search
USPC .................... 585/319, 323, 401, 701
See application file for complete search history.

(56) References Cited

U.S. PATENT DOCUMENTS

| | | | |
|---|---|---|---|
| 6,030,521 A | 2/2000 | Jessup et al. |
| 6,187,171 B1 | 2/2001 | Tsuboi |
| 6,238,446 B1 | 5/2001 | Henderson |
| 6,353,143 B1 | 3/2002 | Fang et al. |
| 6,451,075 B1 | 9/2002 | Schoppe et al. |
| 6,565,617 B2 | 5/2003 | Kalghatgi |
| 6,890,423 B2 | 5/2005 | O'Rear |
| 7,833,295 B2 | 11/2010 | Clark |
| 7,897,034 B2 | 3/2011 | De Oliveira et al. |
| 2003/0028058 A1 | 2/2003 | Weissman et al. |
| 2005/0032920 A1 | 2/2005 | Norbeck et al. |
| 2005/0256212 A1 | 11/2005 | Norbeck et al. |
| 2006/0288635 A1 | 12/2006 | Seyfried |
| 2007/0187291 A1 | 8/2007 | Miller et al. |
| 2010/0285576 A1 | 11/2010 | Norbeck et al. |
| 2011/0061290 A1 | 3/2011 | Aulich et al. |
| 2011/0168947 A1 | 7/2011 | Ji et al. |
| 2012/0116137 A1 | 5/2012 | Fang et al. |

*Primary Examiner* — Thuan D Dang
(74) *Attorney, Agent, or Firm* — Blank Rome LLP

(57) ABSTRACT

This invention relates to fuel compositions for use in combustion engines, such as for motor vehicle and aircraft usage. The fuel composition contains at least 99.5% of aromatic hydrocarbons and paraffinic hydrocarbons. The composition also preferably contains no lead, no multi-ring compound (only single ring compounds are present), less than about 15 ppm sulfur, and/or less than about 5 ppm nitrogen species. The resulting fuel is a drop-in fuel that provides clean burning with little to no engine deposit, high lubricity, high stability, and low corrosion.

11 Claims, 3 Drawing Sheets

Figure 1 - GC-MS spectra of synfuel samples under different conditions of MTGH process
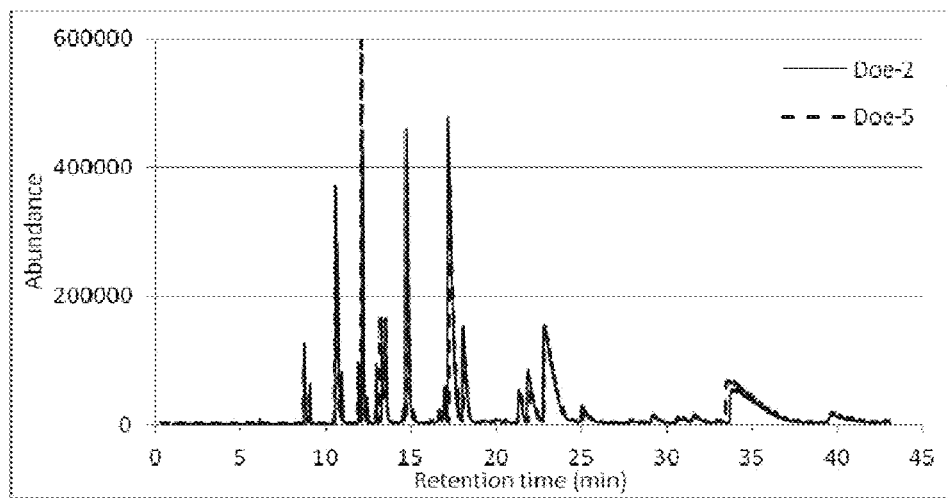

Figure 2 - Recirculation rate effect on synfuel composition
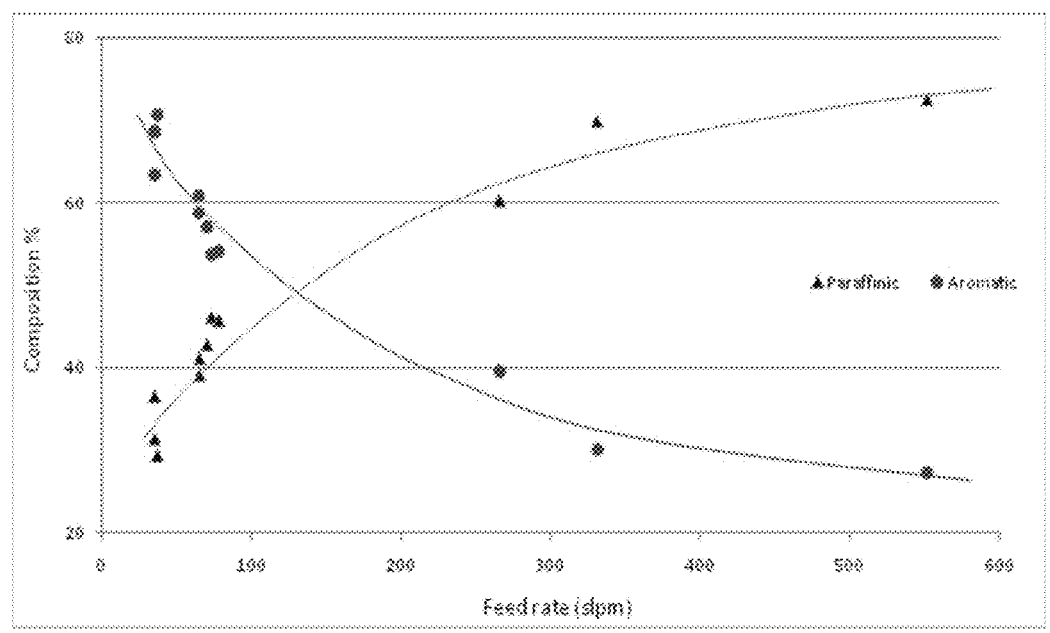

Figure 3 – D-86 data of typical synfuel in a comparison with commercial gasoline
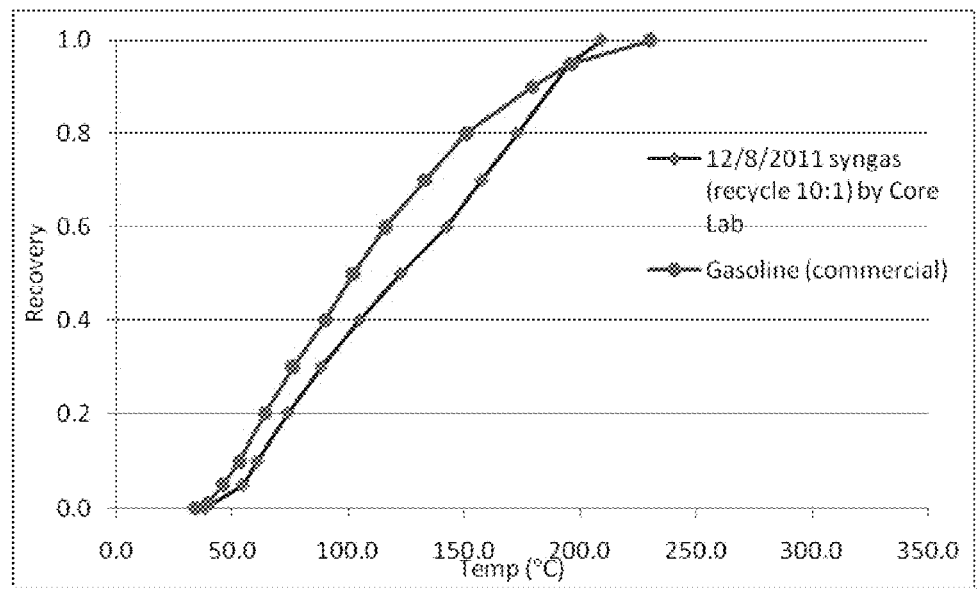

FUEL COMPOSITION

This application is a divisional application of U.S. patent application Ser. No. 13/547,826, filed Jul. 12, 2012, which is incorporated herein by reference.

FIELD OF THE INVENTION

This invention relates to fuel compositions for use in combustion engines, such as for motor vehicle and aircraft usage.

BACKGROUND OF THE INVENTION

The declining trend of fossil fuel reserves and the pollution detriment caused by fossil fuel burning has brought the development urgency for the renewable green energy. Among all renewable resources, biomass is the only carbon source which can be converted into solid, liquid and gaseous products through pyrolysis/gasification processes. However, processes for making fuel from biomass, e.g. the Mobile traditional methanol-to-gasoline process, produce high concentration of multi-ring durene and other multi-methyl substituted aromatic compounds that result in undesired soot formation and engine deposit. For biodiesel fuels derived from fatty acid methyl esters (FAME), their higher surface tension, lower volatility and higher specific gravity lead to larger droplet size and thus more wall impingement of the fuel during injection in the combustion chamber. This results in higher levels of fuel dilution as the oil is scraped down into the crankcase by the scraper ring.

Additionally, one of the major environmental problems confronting the United States and other countries is atmospheric pollution (i.e., "smog") caused by the emission of gaseous pollutants in the exhaust gases from automobiles. This problem is especially acute in major metropolitan areas, such as Los Angeles, Calif., where the atmospheric conditions and the great number of automobiles account for aggravated air pollution. It is well known that the three primary gaseous constituents, or pollutants, which contribute to air pollution due to auto exhaust are nitrogen oxides (NOx), carbon monoxide (CO), and unburned or incompletely burned hydrocarbons (i.e., hydrocarbon components originally present in the gasoline fuel which are not fully converted to carbon monoxide or dioxide and water during combustion in the automobile engine). Considerable efforts have been spent through a partnership including resources of government, industry and institute of higher learning to significantly reduce $NO_x$ (nitrogen oxides), $CO_x$ (carbon oxides) and PM (particulate matter) emissions while maintaining the superior advantage in fuel economy of road vehicles. As such, Congress and regulatory authorities, such as CARB (the California Air Resources Board), have focused on setting specifications for low emissions gasoline and diesel. The specifications, however, require the presence of oxygenates in gasoline sold in areas that are not in compliance with federal ambient air quality standards for ozone, and the degree of non-attainment is classified as severe, or extreme. Among the emissions which the reformulated gasoline is designed to reduce, are $NO_x$, hydrocarbons, and toxics (benzene, 1,3-butadiene, formaldehyde and acetaldehyde). A reduction in these emissions has been targeted due to their obvious impact upon the air we breathe and the environment in general.

Therefore, there is a need for clean burning synthetic fuel (synfuel) that meets regulatory requirements. This is especially advantageous when the fuel can be made directly without being blended.

SUMMARY OF THE INVENTION

The present invention relates to a fuel composition that contains at least 99.5% of aromatic hydrocarbons and paraffinic hydrocarbons. The composition also preferably contains no lead, no multi-ring compound (only single ring compounds are present), less than about 15 ppm sulfur, and/or less than about 5 ppm nitrogen species. The resulting fuel is a drop-in fuel that provides clean burning with little to no engine deposit, high lubricity, high stability, and low corrosion.

The present invention also relates to a method to control the aromatic to paraffinic ratio of the fuel composition using a synthetic process. The process is disclosed in U.S. patent application Ser. No. 12/942,680, filed Nov. 9, 2010, which is incorporated herein by reference. In summary, the process entails four sequential catalytic stages (R-1, R-2, R-3, and R-4) with intermediate heat exchange to provide the requisite temperature in each stage, but with no interstage separation (the process is also referred to herein as the "MTGH process"). Applicants have discovered that the aromatic to paraffinic ratio of the fuel produced by the process can be controlled by varying the total syngas flow rate into R-1. The higher the circulation rate, the lower the aromatic to paraffinic ratio.

BRIEF DESCRIPTION OF THE DRAWINGS

FIG. 1 is graph of the GC-MS spectra of two different synfuel samples (DOE-1 and DOE-2) produced using the MTGH process.

FIG. 2 is a graph showing the circulation rate dependence of the synfuel composition produced from the MTGH process.

FIG. 3 is a distillation behavior comparison of the MTGH synfuel and commercial gasoline.

DETAILED DESCRIPTION OF THE PREFERRED EMBODIMENT

This invention relates to fuel compositions for use in combustion engines, such as for motor vehicle and aircraft usage. The fuel can be used as a drop-in fuel that provides clean burning with little to no engine deposit, high lubricity, high stability, and low corrosion. The fuel composition that contains at least 99.5% (by weight of the total composition) of aromatic and paraffinic hydrocarbons. The composition also preferably contains no lead, no multi-ring aromatic compounds (only single ring aromatics are present), less than about 15 ppm sulfur, and/or less than about 5 ppm nitrogen species.

In preferred embodiments, the paraffins include normal or branched C4 to C7 paraffins , dimethyl cyclopentane, dimethyl cyclohexane, and combinations thereof. Further, the aromatics include toluene, xylenes, trimethyl benzenes, tetramethyl benzenes (including durene), and combinations thereof. The paraffin hydrocarbons and aromatics, together, make up at least 99.5% of the fuel composition. Preferably, the fuel composition contains at least 99.5% of (1) C4-C7 of both the normal and the branched paraffinic components (such as straight hexane and iso-hexane); (2) C6-C8 of single cyclic ring paraffins (such as methyl cyclohexane and dimethyl cyclopentane); and (3) C7-C10 single phenyl ring with methyl-, ethyl- and propyl-substituted aromatics (such as xylenes and trimethyl benzenes). More preferably, the C4-C7 normal and branched paraffinic components is present in the range of 30-60% (by weight of the total composition); the C6-C8 of single cyclic ring paraffins is present in the range of 10-20%; and the C7-C10 single phenyl ring with methyl-, ethyl- and propyl-substituted aromatics is present in the range of about 20-60%.

The remaining 0.5% or less of the fuel composition can include minor component that are generally found in gasoline. Those minor components include, but are not limited to, sulfur species, nitrogen species, multi-ring cyclic (e.g. decalin), and other olefins. Due to the low sulfur and nitrogen contents, as well as the lack of multiple ring aromatics, the use of the fuel composition generates less soot in tailpipe emission. Its trend in deposit and gum formation in fuel circulation system is also low, resulting in much clean fuel injector. For high-pressure diesel injector system, deposits on internal injector components and assemblies can adversely affect injector dynamics, emission regulations and fuel economy performance. In diesel engines, the fuel requirements in injector cleanliness and deposit resistance are in strong demand.

The fuel composition of the present invention can be produced synthetically from synthetic gas (syngas) using the process disclosed in U.S. patent application Ser. No. 12/942,680 ("'680 Application"), filed Nov. 9, 2010, which is incorporated herein by reference. That process involved four sequential catalytic stages with intermediate heat exchange to provide the requisite temperature in each stage, but with no interstage separation (the process is also referred to herein as the "MTGH process"). The first reactor (R-1) converts synthesis gas to principally methanol and some water. The product from the first reactor 1, a vapor mixture of essentially methanol, water and unreacted synthesis gas, flows through conduit 10 to a second reactor 2 (R-2). The second reactor converts a portion of the methanol to dimethylether. The product from second reactor, which essentially contains methanol, dimethylether, water and unreacted synthesis gas, flows via conduit 11 to a third reactor (R-3). The third reactor converts methanol and dimethylether to fuel product (gasoline, jet fuel and/or diesel) and heavy gasoline. The product from the third reactor 3 contains essentially fuel product (C4-C8 hydrocarbons, toluene, and xylene), heavy gasoline (≥C8 aromatics) and water, with minor amounts of unreacted methanol and dimethylether and unreacted synthesis gas. This product flows via conduit 12 to a fourth reactor 4 (R-4) to convert the heavy gasoline to a product containing the fuel composition with low heavy gasoline content, water, minor amounts of unreacted methanol and dimethylether and unreacted synthesis gas. The fuel composition can then be separated from the water, the light gases (including light paraffins below C4), and unreacted syn gas using a separator. Other variations and specific embodiments of the MTGH process disclosed in the '680 Application are appropriate for the present invention.

In another embodiment of the present invention, the ratio of aromatics to paraffins in the fuel composition can be controlled by the total flow rate of syngas entering the reactor R-1. This total flow rate includes the syngas entering R-1 from the gasifier that produces the syngas from biomass, and the unreacted syngas that is recycled during the MTGH process. Because it is relatively difficult to change the flow rate coming from the falsifier, the syngas recycling rate is preferably used affect the total flow rate of syngas entering R-1. Syngas recycling can be used to increase the product yield. Because the conversion efficiency of R-1 is not high (approximately 15%), the unreacted syngas can be recycled back into R1.If the recycling rate is increased, the mass flow rate within all reactors would increase. The syngas can be recycled from any of the four reactors in the MTGH process (R-1, R-2, R-3, or R-4). Preferably, the unreacted syngas from R-4 is recycled to R-1. Essentially, the higher the rate for syngas fed into R-1, the higher the ratio of paraffins to aromatics. Preferably, the ratio of aromatics to paraffins in the inventive composition is about 0.5:1 to 2.4:1.

The relationship between total syngas flow rate into R-1 and aromatics/paraffins ratio greatly simplifies the operation of the MTGH process. In operation, a desired aromatics/paraffins ratio can be achieved by determining the ratio at the process output, and increasing the total syngas flow rate into R-1, if more aromatics are desired (or decreasing the flow rate if more paraffins are desired). The total flow rate can be increased or decreased stepwise until the desired ratio is achieved. Preferably, the total flow rate is adjusted by increasing or decreasing the syngas recycling rate. Alternatively, a graph similar to FIG. 2 could be generated for the process and used to determine the feed rate to achieve the desired aromatics/paraffins ratio.

In addition to producing the fuel composition of the present invention, the MTGH process can be used to prepare high aromatics content by operating at low feed rate to produce aromatics for certain chemical applications requiring aromatic-rich stream. For example, di-acids can be generated through ortho- or para-xylenes to form bridging groups suitable for polymer crosslinks.

EXAMPLE 1

Analysis of Fuel Product

A fuel was produced by the MTGH process. Quantification of the fuel was determined by both GC-MS and IR techniques. For GC-MS measurement, a fixed volume of 1 μl of the sample is injected into the port and the speciation quantity is characterized by quadruple mass filter. The reproducibility of the syringe is reasonably accurate and the volume fluctuation cannot exceed an uncertainty level more than 5%. The major change for a specific species in the mass count comes from the variation of catalyst used in R4.The relative change between the paraffinic and aromatic portions comes from the feed rate of the syngas during the MTGH process.

The distribution of the product shows a relatively narrow window containing (1) C4-C7 of both the normal and the branched paraffinic components (such as straight hexane and iso-hexane); (2) C6-C8 of single cyclic ring paraffins (such as methyl cyclohexane and dimethyl cyclopentane); and (3) C7-C10 single phenyl ring with methyl-, ethyl- and propyl-substituted aromatics (such as xylenes and trimethyl benzenes). The single ring nature for both the cyclic and the aromatic portions is related to the geometric (tunnel/cage) configurations of the zeolite catalyst. In general, iso-paraffins always come earlier than the normal paraffins and cyclics always come earlier than aromatics in GC column. The aromatics follow the sequence from one methyl-substituted to two-methyl, three-methyl and higher-methyl substitutions. In analysis, we normally group iso- and normal-hydrocarbons together for simplicity. All isomers of xylenes (ortho-, meta- and para-xylenes) and tri-methyl benzenes are grouped together. All paraffinic portions (from C4 to cyclics) and all aromatic portions (from toluene to durene) can be summed up to get the [aromatic]/[paraffinic] ratio. This ratio varies with operation conditions. For constant temperatures and pressure in reactors, the ratio is a sensitive function of feed rate of the syngas into R-1.

Table 1 lists the retention time data for major species within the synfuel produced by the MTGH process. In contrast to gasoline refined from crude oil, the distribution encompasses a relatively narrow range of species. The aliphatic portion ranges from C4 to C7 containing both straight and iso-configurations. The iso portion is always in higher abundance than the normal species. Aliphatic C8 can be barely seen around the time of 13.8 minute with low abundance. The group of cyclic paraffins such as cyclohexane begins to show at 12 minute and the most abundant methyl-substituted cyclopentanes and cyclohexanes are located around the time of 12.16~13.53 minute. All aromatics contain only one ring (no multi-ring aromatics) and the species with multiple rings are absent in the synfuel. The one ring configuration can be attributed to the limit of pore shape in the zeolite catalyst. The retention time follows the number of methyl substitutions on phenyl ring such as toluene (one-methyl) at 15.22 minute, xylenes (two-methyls) at 18.1 and 18.9 minutes, trimethyl benzene (three-methyls) at 23.3/24.1/25.8 minutes, and tetramethyl benzene (four-methyls) at 36~40 minutes. Pentamethyl and hexamethyl substituted benzenes, if any, are seldom seen. When we sum up all aliphatic and aromatic species, we can get the ratio between paraffins and aromatics. The distribution is obviously a function of operation parameters of temperature, pressure and catalyst types, particularly the catalyst used in R-4. For example, when hydrogenation catalyst such as Co-Molybdenum is used in R-4, the contents of toluene and xylenes become high. When hydrocracking catalyst such as Ni-based catalyst is used, the iso-aliphatic portions become high.

TABLE 1

| Species | Retention time (minutes) |
| --- | --- |
| i-C4 | 5.64 |
| C4 | 6.28 |
| i-C5 | 8.91 |
| C5 | 9.25 |
| i-C6 | 10.83/10.91 |
| C6 | 11.15 |
| Dimethyl cyclopentane | 12.16 |
| i-C7 | 12.41 |
| C7 | 12.63 |
| Dimethyl cyclohexane | 13.53 |
| Toluene | 15.22 |
| Xylenes | 18.1/18.9 |
| Trimethyl benzenes | 23.3/24.1/25.8 |
| Durene + tetramethyl benzenes | 36-40 |

EXAMPLE 2

Feed Rate Dependence of the Aromatic to Paraffinic Ratio

In order to investigate the composition response relative to operation parameters, series of runs with design-of-experiment (DOE) was conducted. A typical comparison between DOE-2 and DOE-5 is shown in FIG. 1. All paraffinic (from C4 to cyclics) and aromatic portions (from toluene to durene) can be summed up to get the aromatic/paraffinic ratio. The feed rate dependence of the aromatic/paraffinic ratio is shown in FIG. 2.

EXAMPLE 3

Physical Characteristics of the MTGH Synfuel

The synfuel composition can be well controlled by our MTGH system and shows good cold flow properties. Based on CFPP (cold filter plugging point) test, the starting temperature for filter plugging for most biodiesels occurs high, way above −10° C. Such high freezing point in biodiesel excludes its applications as Diesel #1 and jetfuel, even with addition of excessive viscosity depression additives. Another drawback of biodiesel is their poor wear scar data in HFRR (high frequency reciprocating rig) test. This is due to the polar nature of methyl ester towards metal surface as well as some high-affinity hydroxyl impurities containing within biodiesel which tend to decompose to form wearing species at asperity areas. Fatty acids with different degrees of unsaturation can react with metal ion impurities to form metal soap. Although the maximum requirement for the wear scar in D975 is 520 µm, a trend for tighter limit of 400 µm is proposed. In terms of fuel quality, Table 2 lists the results of some additional tests. The MTGH fuel shows much better low temperature flow properties. As shown in Table 2, the light end (paraffinic rich synfuel) portion shows −51° C. for CFPP. When depression additive is required in certain low temperature application, the amount is definitely much less than biodiesel. The wear response of MTGH fuel is also excellent because it doesn't contain any surface-sensitive, easily decomposed multiple-ring components.

TABLE 2

| ASTM test | Result |
| --- | --- |
| D-3606 for [benzene] | <0.28% v |
| D-5191 vapor pressure | 2.89 psi |
| Octane number | 93 |
| D130 Cu-corrosion test | 1a |
| D525 induction time for oxidation test | >240 minutes |
| D6371 for CFPP (cold filter plug point) | −27° C. for heavy end −51° C. for light end |

Consistent with GC-MS data where very little (less than 0.28%) benzene is present, only methyl-substituted benzenes are observed in MTGH synfuel. Due to the rich nature of one-ring aromatics, the vapor pressure is reasonably low and the octane number is high. Due to the fact that the synfuel is directly derived from syngas, little S- and N-containing species are present so that the Cu-strip corrosion test should be favored. The MTGH synfuel is also oxidatively stable where a relatively long induction time is observed in D525 test. It is known that the deposit formation in fuel is mainly derived from fuel instability upon thermal/oxidative heating. When fuel is oxidatively unstable, the acid formation may interact with metal surface to form carboxylate soaps which are known to be bad actors for deposit formation. The small number of species in MTGH synfuel composition, when compared to refined gasoline, should make the fuel cleaner and more stable in vehicle applications. The distillation behavior can be easily evaluated by D-86. A comparison of D-86 response between the commercial gasoline and MTGH synfuel is shown in FIG. 3. The separation of T50 between these two fuels is differed within a range of 25° C.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for controlling aromatics to paraffins ratio in a MTGH process comprising the steps of:

a. determining the aromatics to paraffins ratio of an outlet stream of the process; and
b. adjusting the aromatics to paraffins ratio by varying the total syngas flow rate into a first reactor of the MTGH process.

2. The method of claim 1, wherein the total syngas flow rate is increased to decrease the aromatics to paraffins ratio of the outlet stream.

3. The method of claim 1, wherein the total syngas flow rate is decreased to increase the aromatics to paraffins ratio of the outlet stream.

4. The method of claim 1, wherein step b is performed to attain a desired aromatics to paraffins ratio.

5. The method of claim 4, wherein the desired aromatics to paraffins is about 0.5:1 to about 2.4:1.

6. The method of claim 1, wherein the aromatics contain toluene, xylene, trimethyl benzene, durene, and/or tetramethyl benzene.

7. The method of claim 1, wherein the paraffins contain normal or branched C4-C7 paraffins and C6-C8 single cyclic ring paraffins.

8. The method of claim 1, wherein the aromatics and paraffins together make up 99.5% of a synthetic fuel.

9. The method of claim 8, wherein the synthetic fuel contains containing no significant amount of lead, less than about 15 ppm sulfur, and/or containing less than about 5 ppm nitrogen species.

10. The method of claim 7, wherein the C6-C8 of single cyclic ring paraffins contain dimethyl cyclopentane and dimethyl cyclohexane.

11. The method of claim 8, wherein the paraffinic hydrocarbon consists of C4 paraffins, C5 paraffins, C6 paraffins, dimethyl cyclopentane, C7 paraffins, and dimethyl cyclohexane; and the aromatic hydrocarbon consists of toluene, xylene, trimethyl benzene, durene, and tetramethyl benzene.

* * * * *